(12) United States Patent
Lee et al.

(10) Patent No.: US 10,345,269 B2
(45) Date of Patent: Jul. 9, 2019

(54) THREE-DIMENSIONAL ULTRASONIC WAVE VELOCITY TEST SYSTEM

(71) Applicant: CHESAPEAKE ENERGY CORPORATION, Oklahoma City, OK (US)

(72) Inventors: Ji Soo Lee, Oklahoma City, OK (US); John Brumley, Norman, OK (US); Evan Morgan, Edmond, OK (US); Lance DeSpain, Oklahoma City, OK (US)

(73) Assignee: Chesapeake Energy Corporation, Oklahoma City, OK (US)

( * ) Notice: Subject to any disclaimer, the term of this patent is extended or adjusted under 35 U.S.C. 154(b) by 110 days.

(21) Appl. No.: 15/670,353

(22) Filed: Aug. 7, 2017

(65) Prior Publication Data

US 2018/0045683 A1 Feb. 15, 2018

Related U.S. Application Data

(60) Provisional application No. 62/373,781, filed on Aug. 11, 2016.

(51) Int. Cl.
*G01L 1/25* (2006.01)
*G01N 29/04* (2006.01)
(Continued)

(52) U.S. Cl.
CPC .............. *G01N 29/07* (2013.01); *G01L 1/255* (2013.01); *G01N 29/043* (2013.01); *G01N 29/11* (2013.01); *G01N 29/44* (2013.01)

(58) Field of Classification Search
CPC ...... G01N 29/043; G01N 29/07; G01N 29/11; G01N 29/44; G01L 1/255
(Continued)

(56) References Cited

U.S. PATENT DOCUMENTS

| 5,631,423 | A | * | 5/1997 | Rhodes | .................. | G01H 13/00 |
| | | | | | | 73/579 |
| 2004/0025596 | A1 | * | 2/2004 | Tegtmeier | ............. | G01L 5/0004 |
| | | | | | | 73/789 |

(Continued)

FOREIGN PATENT DOCUMENTS

JP 61254849 * 11/1986

OTHER PUBLICATIONS

5th Pan American Conference for NDT, Cancun, Mexico, Evaluation of the wave speed for LCR waves in Composites, Tainá Gomes Rodovalho*, Oct. 2-6, 2011.*

*Primary Examiner* — Jacques M Saint Surin
(74) *Attorney, Agent, or Firm* — McAfee & Taft (57) ABSTRACT

A system for and a method of measuring ultrasonic wave velocities in a subterranean core specimen is provided. Ultrasonic wave velocities are measured from the side surfaces (faces) of a polygonal-shaped core specimen having at least ten sides or faces. Stress is introduced to the core specimen by hydraulic rams associated with each set of opposing sides. As stress is applied, ultrasonic waves are introduced to at least one side of the set of opposing sides and the wave transmitted through the core specimen is measured. Subsequently, the wave velocity for the ultrasonic wave can be calculated based on the measurements taken. Also, elastic properties associated with the core specimen can be calculated.

17 Claims, 9 Drawing Sheets

(51) Int. Cl.
*G01N 29/11* (2006.01)
*G01N 29/44* (2006.01)
*G01N 29/07* (2006.01)

(58) Field of Classification Search
USPC .......................................................... 73/597
See application file for complete search history.

(56) References Cited

U.S. PATENT DOCUMENTS

| | | | |
|---|---|---|---|
| 2004/0187597 A1* | 9/2004 | Romano | G01N 3/10 73/856 |
| 2005/0247137 A1* | 11/2005 | Nickerson | G01N 11/142 73/846 |
| 2011/0120209 A1* | 5/2011 | Rose | G01M 3/243 73/1.82 |
| 2012/0031193 A1* | 2/2012 | Adams | G01L 25/00 73/804 |
| 2015/0160091 A1* | 6/2015 | Du | G01P 5/14 73/40 |

\* cited by examiner

THREE-DIMENSIONAL ULTRASONIC WAVE VELOCITY TEST SYSTEM

CROSS-REFERENCE TO RELATED APPLICATIONS

This application claims the benefit of U.S. Provisional Application No. 62/373,781 filed Aug. 11, 2016, which is hereby incorporated by reference.

FIELD

The present disclosure relates generally to measurements of properties of specimens from subterranean formations, and more specifically, to measurements of stress-dependent acoustic anisotropy or stress dependent anisotropy in acoustic wave velocities and elastic properties in specimens from unconventional formations.

BACKGROUND

Unconventional formations such as shale contain bedding planes and laminations along the horizontal direction. Such geological discontinuities influence acoustic wave velocities depending on the orientation of wave to the discontinuities. When an acoustic wave travels parallel to discontinuities in a formation, the wave velocity becomes faster. If the wave travels perpendicular to them, the wave speed is attenuated. In addition, in-situ stress conditions change wave velocities. Acoustic wave velocities can be investigated by a stress-dependent acoustic anisotropy test, which is considered a special, advanced rock physics experiment. In fact, it is important to measure acoustic wave velocities at various orientations and stress conditions for improving current formation evaluations, reservoir characterizations, horizontal drilling, and hydraulic fracturing technologies.

Figure 1:
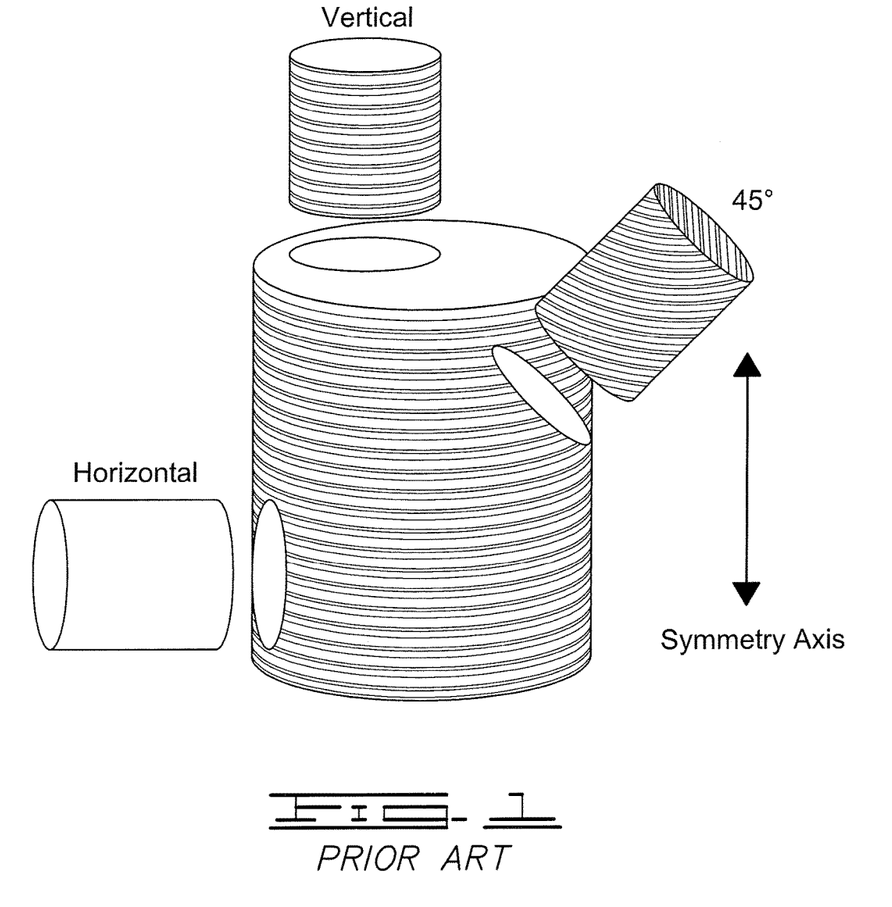
FIG. 1 illustrates a prior art approach where three plug specimens are taken from a whole core.
Figure 2:
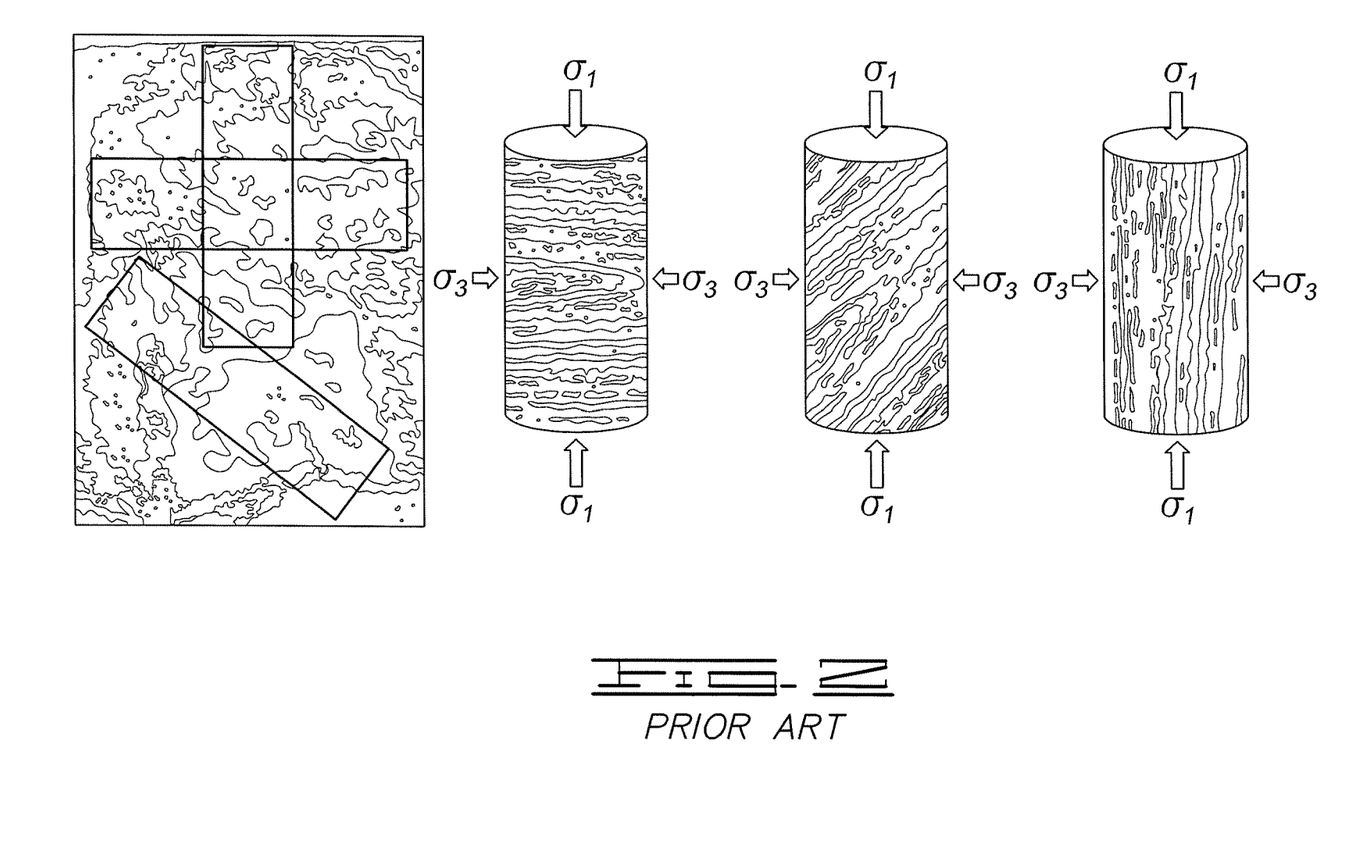
FIG. 2 illustrates a prior art approach where three plug specimens are taken from a ⅔ butt section core.

Past stress-dependent acoustic anisotropy test suffered from substantial limitations. First, specimen preparation has been restricted to preparing standardized specimens from shale formations. The conventional approach for plug sample specimens is to use a minimum of three plug specimens taken at the vertical, 45° and horizontal directions. FIGS. 1 and 2 illustrate prior art approaches where three plug specimens are taken from either a whole core (FIG. 1) or ⅔ butt section core (FIG. 2) to measure acoustic anisotropy along the vertical, 45° and horizontal directions. Each plug is used for a dynamic triaxial compressive test under various differential stresses. If a rock is a conventional rock such as sandstone, then the core specimen can allow getting all three plugs at an adjacent spot with the same depth and same lithology, because the condition of the rock is relatively homogeneous and isotropic.

This plug specimen approach can be problematic in anisotropic materials such as shale. In shale and other anisotropic materials, tight spacing of horizontal laminations does not allow having vertical and 45° specimens. Rather, it is usually impossible to get all plugs at the same spot. Thus, if plugs specimens are taken according to the above procedures, the plug specimens might be scattered along ±1 foot distance. Often, the testing plan needs to skip certain depths due to the lack of specimens.

Second, the current laboratory equipment for these tests relies on the assumption that measurements of ultrasonic wave velocity in each opposite direction must be equivalent. This assumption rests on the material being a continuum material; that is, the material not having microcracking, particle motion, and other defects that would make it anisotropic. However, this assumption is not generally true. Natural rocks are discontinuum materials because of the existence of various geologic discontinuities such as joints, faults, dykes, veins, bedding planes, laminations, foliations, gneissosity, shistosity, lineation, pores, voids, and other natural weaknesses within the rock.

Figure 3:
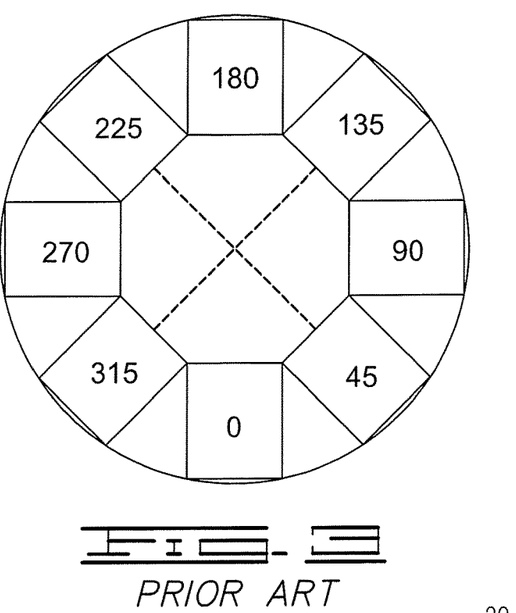
FIG. 3 illustrates a prior art approach of selecting sites for taking eight plug specimens from a whole core.

To overcome the assumption of a continuum material, some approaches have proposed taking eight plug specimens from a whole core in order to study anisotropy with every 45°. As illustrated in FIG. 3, these approaches take eight short plugs of core specimens and the remaining core material is discarded. FIG. 3 shows the site selection for obtaining the plugs from a whole core (section). Thus, these approaches result in eight core specimens, each of which has to be tested. While the intent of this approach is good in terms of anisotropy measurement, this approach is often impractical or even unworkable for the reasons described above, i.e. it is usually impossible to get multiple plug specimens from the same spot for anisotropic or discontinuum materials, such as shale.

Accordingly, a system for performing a three-dimensional stress-dependent ultrasonic wave velocity test that overcomes the current limitations in terms of using an anisotropic specimen, especially one shale specimen per formation, and applying three-dimensional stress with different orientations would be advantageous.

SUMMARY OF THE INVENTION

In accordance with one set of embodiments of the invention, there is provided a method of measuring wave velocities in a subterranean core specimen (sometimes referred to as a sample) having a bedding plane direction. The method comprises the step of introducing the core specimen into a testing system. The core specimen is a polygonal-shaped specimen having at least ten faces such that each face has an associated opposing face to form at least five sets of opposing faces. The testing system comprises a transducer associated with each face of the polygonal-shaped specimen. Subsequently, stress is applied to each face of the polygonal-shaped specimen. The stress is applied by a plurality of rams with each ram being associated with one of the faces of each set of opposing faces such that the same or different stress can be applied to each set of opposing faces. The stress applied to each face is monitored, such as by a load cell. As the stress is applied, an ultrasonic wave velocity is introduced to at least one face of the polygonal-shaped specimen, and the ultrasonic wave is detected on the associated opposing face. Next, the wave velocity for the ultrasonic wave is calculated based on the detected ultrasonic wave.

In some of these embodiments, the method further comprises cutting the core sample into the polygonal-shaped specimen, wherein two faces run perpendicular to the bedding plane direction and the other faces run parallel to the bedding plane direction. The polygonal-shaped specimen can be saturated with a gas or a liquid prior to introducing the polygonal-shaped specimen into the testing system. In one such embodiment, the polygonal-shaped specimen is saturated with salt water.

In these embodiments, the step of calculating wave velocity can comprise measuring the travel time for each ultrasonic wave, and calculating wave velocity for each ultrasonic wave. Further, the method can include calculating elastic properties associated with the core specimen.

In many embodiments, the step of introducing an ultrasonic wave comprises introducing a plurality of ultrasonic waves to the polygonal-shaped specimen with one of the ultrasonic waves introduced to each face of the polygonal-shaped specimen and each ultrasonic wave is detected on the associated opposing face of the polygonal-shaped specimen. The introduction of the plurality of ultrasonic waves can be performed sequentially or simultaneously among two or more faces of the polygonal-shaped specimen.

In another set of embodiments, there is provided a system for measuring wave velocities in a subterranean core specimen having a bedding plane direction. The system comprises a ram, an acoustic assembly, and a load cell. The ram is configured to apply a stress to a first face of a set of opposing faces of a polygonal-shaped core specimen. The polygonal-shaped core specimen has at least ten faces, and the polygonal-shaped core specimen is such that each face has an associated opposing face to form at least five sets of opposing faces. The acoustic assembly is associated with the set of opposing faces and configured to send an acoustic signal into one of the opposing faces and receive a signal from the other opposing face. The load cell is associated with a second face of the set of opposing faces, and configured to monitor force applied to the polygonal-shaped core specimen by the ram to the first face. The acoustic system can comprise piezoelectric crystals associated with each face of a set of opposing faces. The piezoelectric crystals send and receive acoustic waves across the crystal.

In some embodiments, there is a plurality of rams. Each ram of the plurality of rams is associated in a one-to-one relationship with one of the sets of opposing faces such that each of the rams applies stress to the polygonal-shaped core specimen at one of the faces of the associated set of opposing faces. The rams can be associated with half the faces of the polygonal-shaped core specimen.

BRIEF DESCRIPTION OF THE DRAWINGS

FIG. 6 is a schematic side view of the testing apparatus of FIG. 5.

FIG. 7 is a schematic perspective view of an acoustic platen for perimeter faces that can be used in the testing apparatus of FIG. 5.

FIG. 13 is a schematic illustration of layered rock in a subterranean formation. FIG. 13 is based on Lee, J. S. (2016), "Ultrasonic test redesigns sample geometries, iden- tifies high-resolution anisotropy in shale," *Oil and Gas Journal,* 2016 OGJ October. p. 42-47.

DETAILED DESCRIPTION

In the description that follows, like parts are marked throughout the specification and drawings with the same reference numerals, respectively. The drawings are not necessarily to scale and the proportions of certain parts have been exaggerated to better illustrate details and features of the invention. Where components of relatively well-known designs are employed, their structure and operation will not be described in detail.

This disclosure introduces a new, effective approach to measure stress-dependent anisotropy at three-dimension and Thomsen's anisotropy parameters specializing in unconventional formations. Generally, Thomsen's parameters have been used to quantify seismic and acoustic anisotropy at reservoir in-situ stress conditions for subterranean formation in the exploration and production of petroleum. Further, stress-dependent variations in seismic anisotropy are required to accurately analyze reservoir depletion, subsidence, and production modeling. This invention overcomes the current limitations in terms of using one shale specimen per formation, applying three-dimensional stress with different orientations, and having an option of hydrostatic or deviatoric (differential) stress conditions.

Figure 4:
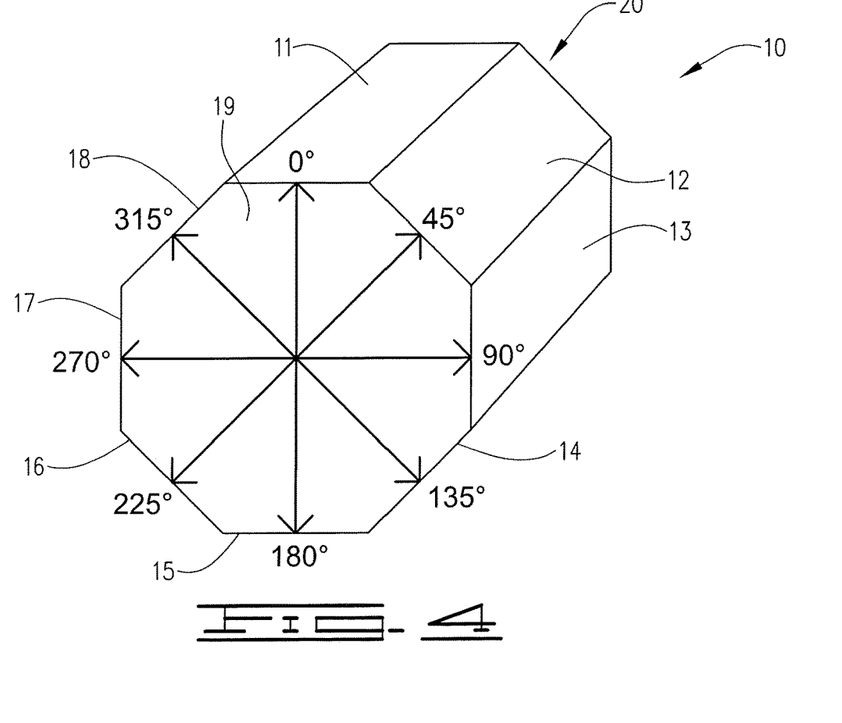
FIG. 4 illustrates a plug specimen useful in certain embodiments. A plug is taken from a whole core and cut into the illustrated octagonal-shaped plug specimen.

This disclosure employs a specimen (sometimes referred to as a "sample") cut into polygonal-shaped specimens having at least ten faces (also referred to as "sides" or "surfaces") such that each face has an associated opposing face to form at least five sets of opposing faces and with two faces running perpendicular to the bedding plane direction (side faces or end faces) and the other faces running parallel to the bedding plane direction (perimeter faces). Typically, the specimen will be cut into an octagonal-shaped specimen. For example, FIG. 4 illustrates an octagonal-shaped specimen 10, which can be produced from a cylindrical plug cut from a ⅔ butt section core. The cylindrical plug can be ground every 45° to make octagonal-shaped specimen 10. A "⅔ butt section core" is a whole core that has been slabbed—cut into two or more specimens longitudinally—into a ⅔ and a ⅓ set. As can be seen from FIG. 4, octagonal-shaped specimen 10 has ten perimeter faces 11 through 18 and has two end faces 19 and 20. Additionally, the faces can be divided into sets of associated opposing faces {11, 15}, {12, 16}, {13, 17}, {14, 18} and {19, 20}.

The perimeter faces 11-18 of octagonal-shaped specimen 10 allow measurements of wave velocities every 45° (FIG. 4) under various stress magnitudes as well as different stress regimes such as hydrostatic and/or deviatoric (differential) loading conditions. Also, end face 19 and end face 20 of octagonal-shaped specimen 10 can be measured; thus, octagonal-shaped specimen 10 provides for ten acoustic anisotropy measurements, a measurement every 45° at the perimeter faces plus measurements at the two end faces. Therefore, all the faces of octagonal-shaped specimen 10 can be measured as a three-dimensional test. In some embodiments, the plug specimen can be cut into polygon-shaped specimens with more faces such as every 30° to produce a dodecagonal-shaped specimen. Measurements for the dodecagonal-shaped specimen can be measured on all 14 faces (twelve perimeter faces and two end faces).

Figure 5:
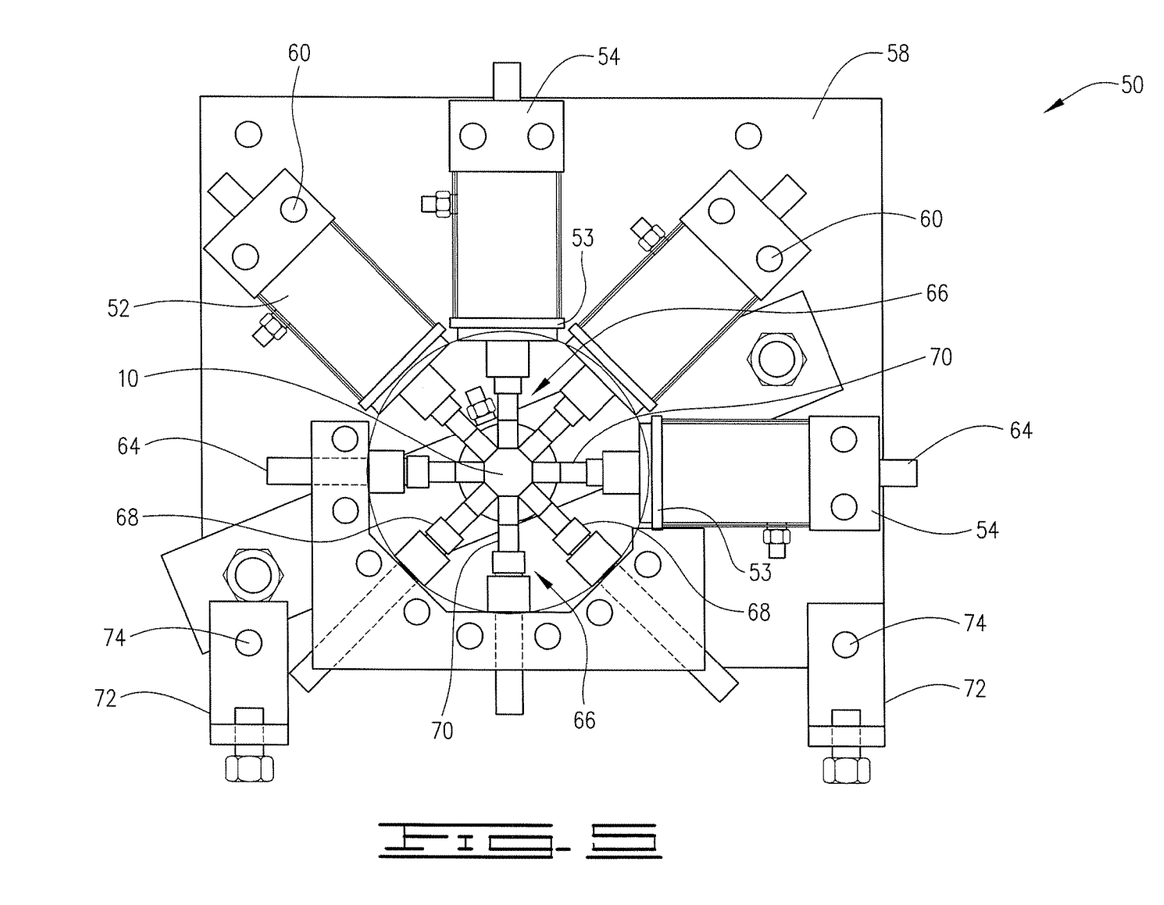
FIG. 5 is a schematic front view of a testing apparatus in accordance with one embodiment.
Figure 8:
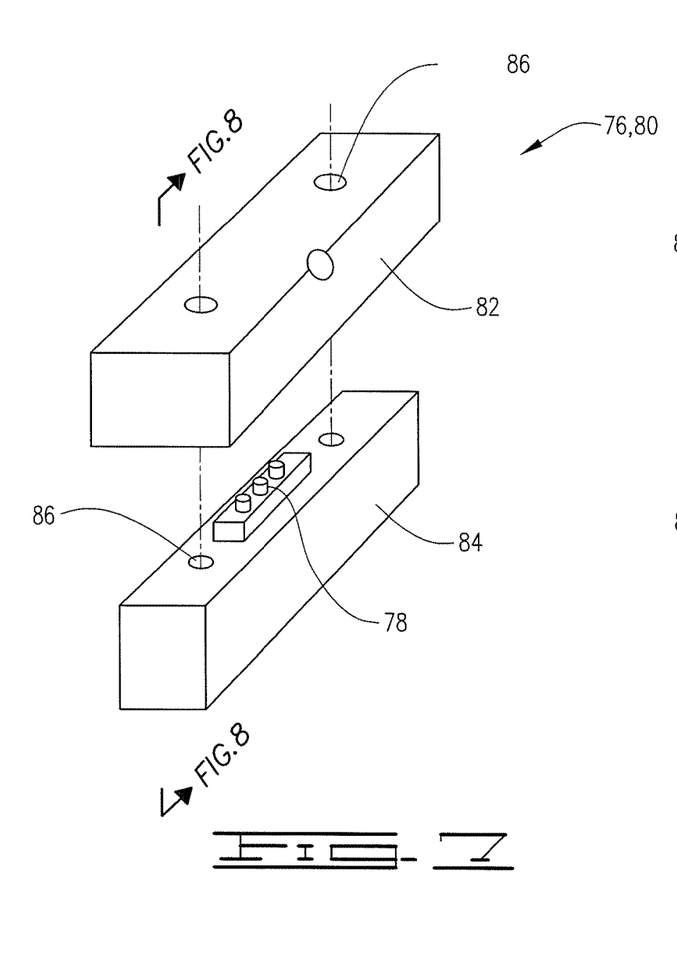
FIG. 8 is an end view of the acoustic platen illustrated in FIG. 7.
Figure 9:
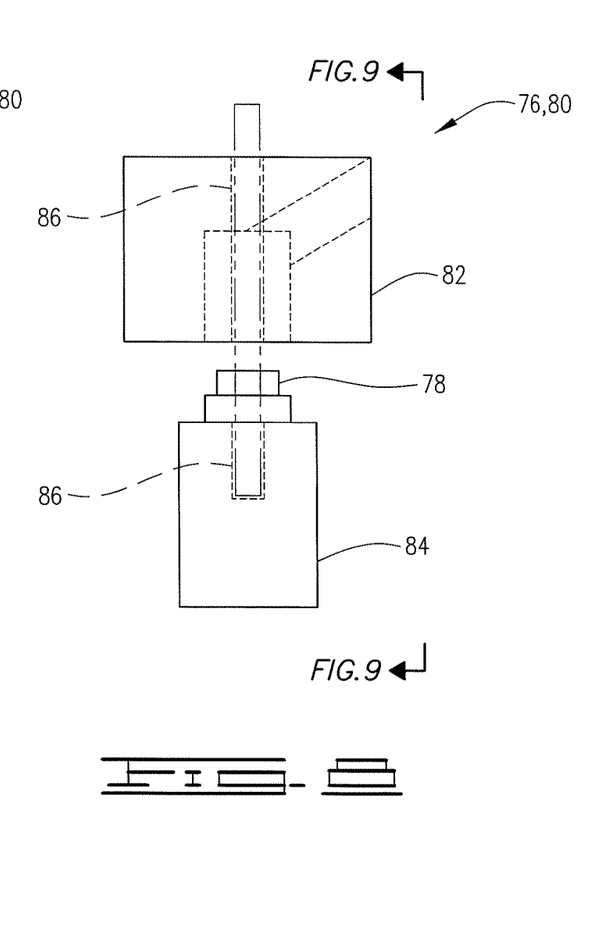
FIG. 9 is a side view of the acoustic platen illustrated in FIG. 7.

Stress testing of the octagonal-shaped specimen can be carried out in the testing apparatus 50 illustrated in FIGS. 5 and 6. Testing apparatus 50 utilizes hydraulic rams 52 to introduce stress to octagonal-shaped specimen 10. While it is within the scope of the invention to use one or more hydraulic rams, presently it is preferred to use one hydraulic ram for each set of opposing faces; thus, maximizing efficiency, eliminating repositioning of the specimen and eliminating associated errors. As illustrated, testing apparatus 50 is configured for testing an octagonal-shaped specimen 10 and utilizes five hydraulic rams, one for each set of opposing perimeter faces and one for the set of opposing end faces.

Hydraulic rams 52 are mounted on reaction blocks 54 and 55, which are mounted on front plate 56 and back plate 58 by thread rods 60 (for hydraulic rams and reaction blocks associated with perimeter faces) and thread rods 62 (for hydraulic rams and reaction block associated with end faces). The hydraulic rams 52 can have collar assemblies 53 to hold the hydraulic ram in position on the reaction blocs 54 and 55. Additionally, hydraulic rams 52 and reaction blocks 54 and 55 can have a cylindrical passage to accommodate threaded adjustment rods 64, which are configured to transmit the ram force to an acoustic assembly stack 66 and specimen surface, and provide a small amount of adjustment for slight specimen dimension variation.

Hydraulic rams 52 have a cylindrical body shape from which the moving plunger is forced out from one of the circular ends. Contact of the moving plunger with specimen 10 would force an unrestrained cylindrical body to move away from the specimen without generating a force on the specimen. The cylindrical bodies of hydraulic rams 52 are held stationary by attachment to reaction block 54 and 55, thus allowing generation of force on the specimen. Reaction blocks 54 are bolted between plates 56 and 58 to provide stability to the complete assembly.

Hydraulic rams 52 can have a passage through the center of the ram body which will allow the passage of a continuous rod, which is threaded adjustment rod 64. Threaded adjustment rod 64 (continuous rod) is employed to transmit the ram force to the platen of the sender/receiver assembly and specimen face, and provide a small amount of adjustment for slight specimen dimension variation.

As utilized in testing apparatus 50, hydraulic rams 52 can provide hydrostatic stress conditions or deviatoric stress conditions. A hydrostatic stress condition is one in which the specimen is subjected to the same stress on all exposed surfaces of the specimen. This can be through applying the same force per unit area on the flat faces by a mechanical means or by sealing the surfaces of the specimen of any shape, placing the sealed specimen in a liquid filled pressure chamber and applying an elevated pressure to the liquid in the chamber.

The hydrostatic stress condition for the proposed design can be achieved by applying the same hydraulic fluid pressures to the hydraulic rams applying force to the perimeter faces (same specimen face area) and different hydraulic pressure on the hydraulic cylinder acting on the end faces as a function of the areas of the different specimen faces and hydraulic cylinder rams.

A deviatoric stress condition is one in which the stress applied to one specimen direction is greater than the forces applied in the other directions. In the present testing system, the deviatory stress can be achieved by using individual pressure sources for each hydraulic cylinder to achieve the various forces required in each specimen direction.

As illustrated in FIGS. 5 and 6, there is a hydraulic ram for each set of opposing faces of the core specimen. This allows testing of the core specimen under both hydrostatic stress conditions and deviatoric stress conditions.

Acoustic assembly stack 66 comprises sender/receiver assembly 70 and in some cases load cell 68. Typically, there will be one load cell 68 per set of opposing faces. Load cell 68 monitors force applied to the specimen surface; in other words, load cell 68 monitors the stress provided to the specimen by hydraulic rams 52. Accordingly, for each set of opposing associated faces, one face will have a hydraulic ram 52 in contact with the face to apply a stress and the opposing associated face will have a load cell in sufficient contact with the surface to measure the stress applied by the hydraulic ram. As illustrated, half of the faces of octagonal-shaped specimen 10 have an associated hydraulic ram and the other half of the faces have an associated load cell. Thus, half the illustrated acoustic assembly stacks 66 comprise load cells 68. Load cells 68 support the sender/receiver assemblies 70 on the faces opposite the hydraulic rams and monitor the magnitude of force being generated by the hydraulic ram.

Sender/receiver assembly 70 is configured to send acoustic wave signals through specimen 10 and to receive or detect acoustic wave signals transmitted through specimen 10. As illustrated, there are sender/receiver assemblies 70 in each acoustic assembly stack 66. This allows both transmission and receiving of acoustic signals at each face of the specimen.

Testing apparatus 50 can be mounted on leveling feet 72, which can be attached by threaded rods 74. As will be realized, threaded rods 60, 62, 64 and 74 can have associated threaded nuts for securing the threaded rods and to allow adjustments, such as adjusting the position of acoustic assembly stack 66.

As illustrated in FIGS. 7 through 12, sender/receiver assembly 70 comprise acoustic platens 76 containing piezoelectric crystals 78. In the illustrated testing apparatus, two different configurations of the acoustic platens 76 are utilized to match the size and shape of the face associated with each acoustic platen 76. Thus, in FIGS. 7, 8 and 9, platen 80 for the perimeter faces comprises an elongated perimeter platen-loading cap 82, which can be rectangular. Elongated platen-loading cap 82 matches the elongated and rectangular shape of the perimeter faces of the octagonal-shaped specimen 10 illustrated in FIG. 4. Cap 82 is mounted on a complementary perimeter platen-contact section 84, and cap 82 can be affixed thereto by screws introduced into screw holes 86. A mounting bracket 88 can be used to mount the platen in testing apparatus 50. As can be seen, a plurality of piezoelectric crystals 78 is contained within acoustic platen 80, to send and receive acoustic waves.

Platen 90 is used for the end faces for the octagonal-shaped specimen illustrated in FIG. 4, and comprises a hexagonal regular polygon shape for platen-loading cap 92 and complementary platen-contact section 94, which can be connected by screws through holes 96. It will be apparent to one skilled in the art that, while matching shapes are preferred, complementary shapes can be used for the platens. Thus, for platen 90 a round or octagonal regular polygon shape could be used.

Figure 10:
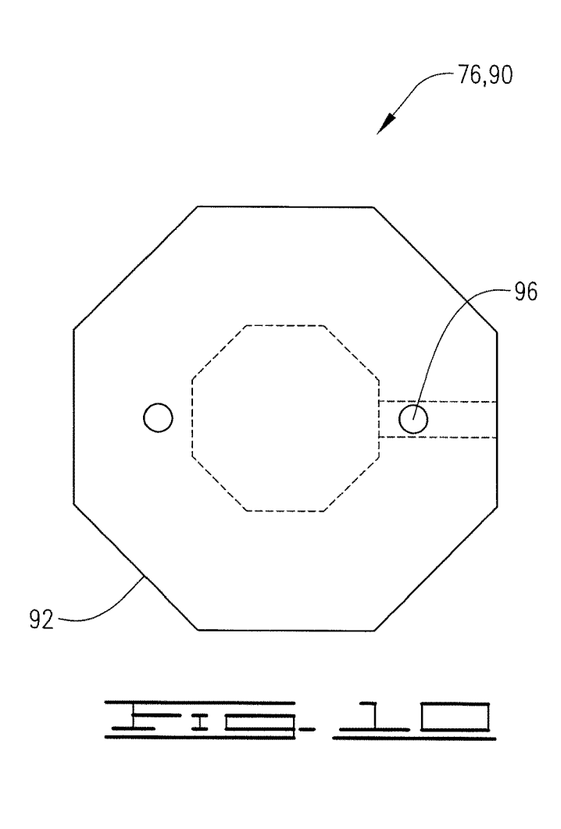
FIG. 10 is a schematic view of an acoustic platen for an end face taken from line 10-10 of FIG. 12. The acoustic platen can be used in the testing apparatus of FIG. 5.
Figure 11:
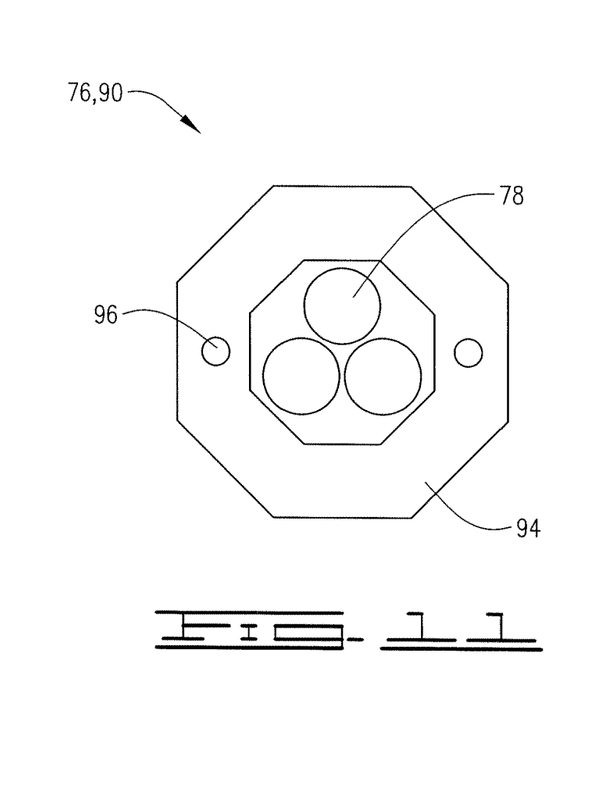
FIG. 11 is a schematic view of the acoustic platen of FIG. 12 taken from line 11-11.
Figure 12:
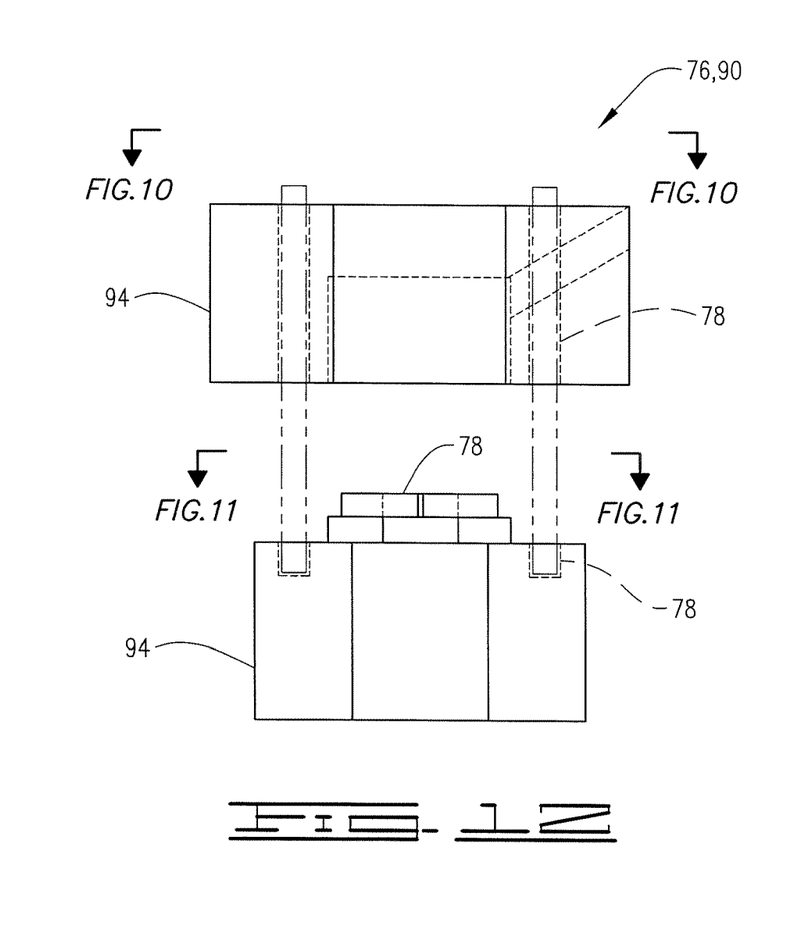
FIG. 12 is a schematic front view of an acoustic platen for an end face.

Like platen 80, platen 90 contains a plurality of piezoelectric crystals 78 as is suitable for sending and receiving acoustic signals through the specimen 10. Typically, three crystals are utilized so as to be able to measure the velocity parallel, perpendicular and 45° to the bedding (30° for a dodecagonal-shaped specimen). Brackets (not shown) can also be used to mount platen 90 in testing apparatus 50.

Two classes of materials are useful for transducing mechanical energy or stress into electrical signals. One class is the piezoelectric materials, which are crystalline substances that develop an electrical polarization proportional to the applied stress. The second class consists of ferroelectric materials which are crystalline substances that can attain a spontaneous and reversible metastable electrical polarization. The electrical response of a ferroelectric substance derives from the stress dependent depolarization of a pre-polarized crystal. The electrical response of piezoelectric materials arises from the stress dependent polarization of a nonpolarized crystal.

The response of either class is referred to as the "piezoelectric" response or the "piezoelectric" effect by those who are experienced in the art. The conversion of mechanical energy or stress to an electrical signal by a piezoelectric crystal is a reversible process. The application of a pulse of direct current voltage to opposing faces of the piezoelectric crystal will cause a force pulse (acoustic energy wave) to be emitted from the crystal.

Piezoelectric crystals which have the polarization perpendicular to the surface of the contact body will generate a compressional acoustic wave. Piezoelectric crystals with the polarization parallel to the surface of the contact body will generate a shear acoustic wave through the body. The magnitude of the electrical signal generated by the "receiving" shear crystal is partially controlled by the degree of alignment between the polarization of the sending and receiving crystals.

Other factors affecting the magnitude of the signal generated by the receiving crystal include (but are not limited to) the voltage magnitude applied to the sending crystal, the duration of voltage applied to the sending crystal, the effectiveness of the material coupling the sender crystal (and receiver crystal) to the specimen body in transmitting acoustic waves, the attributes of the specimen with respect to acoustic wave travel within the specimen (wave energy dissipation, wave attenuation, etc.), and the dimensions of the specimen.

Figure 13:
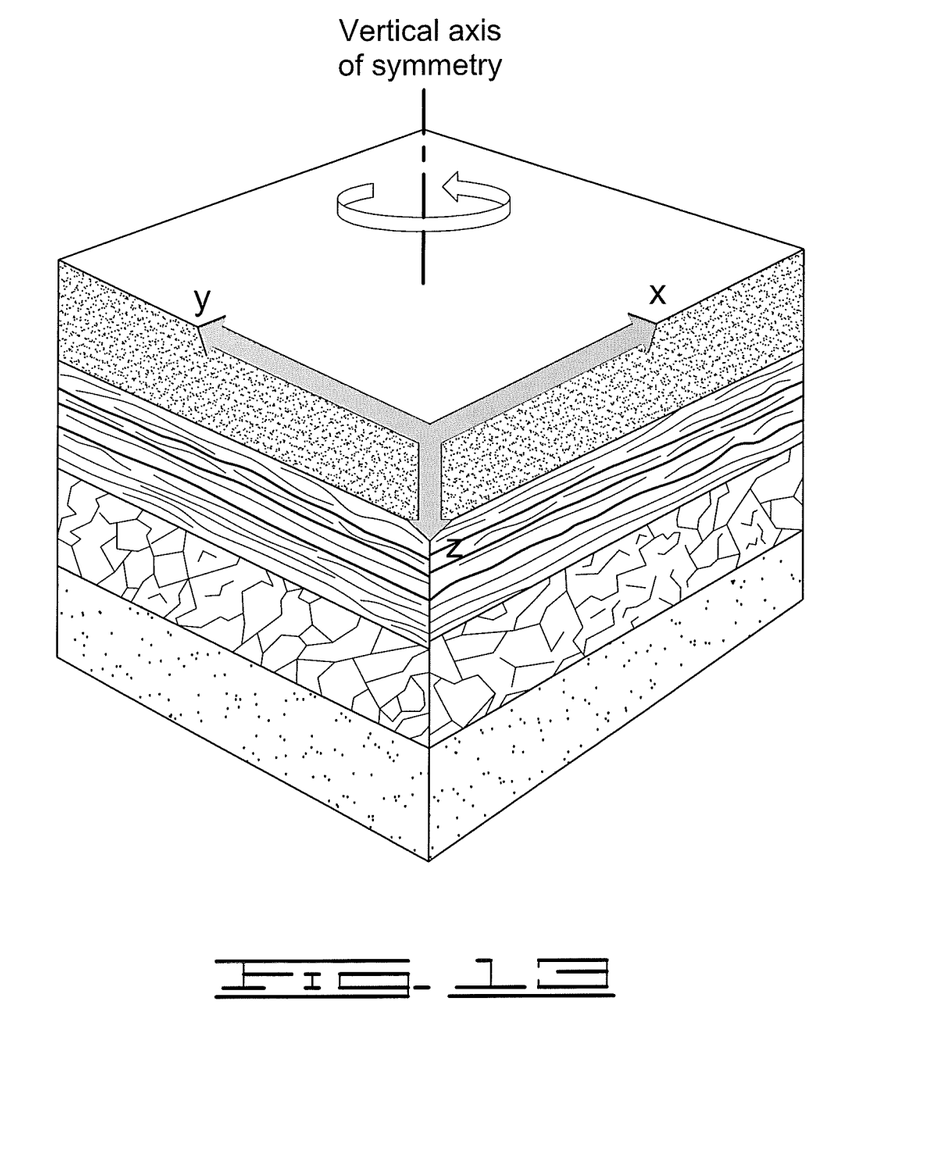

Operation of the testing system first involves cutting a plug specimen from a core taken from a subterranean formation. The plug specimen is cut parallel to the bedding plane direction in the core; that is, the plug specimen is cut along the horizontal direction or perpendicular to the longitudinal axis of core. As shown in FIG. 13, in layered rocks, elastic properties are typically uniform horizontally within a layer (parallel to the bedding plane direction) but may vary vertically and from layer to layer (perpendicular to the bedding plane direction).

Next, the plug specimen is cut and ground every 45° to produce octagonal-shaped specimen 10 illustrated in FIG. 4. It will be noted that each of the eight octagonal faces run parallel with the bedding and each of the two end faces run perpendicular to the bedding. In some embodiments, the plug specimen can be cut and grinded every 30° to produce a dodecagonal-shaped specimen; however, presently the octagonal-shaped specimen with its 45° faces is preferred.

After the octagonal-shaped specimen is produced, the specimen is saturated in a gas or liquid, such as salt water, generally from 1% to 5% KCl solution. The saturation aids in getting a valid Poisson's ratio. Since some tests (such as ultrasonic ⅓ slab test) do not apply high axial stress, specimens can generate extremely low or even negative Poisson's ratio. In order to avoid this, the specimens are saturated. In addition to solutions of salts in water, mineral oil or various gases (such as nitrogen) can be used for saturating the specimens.

After saturation, the specimen is placed into testing apparatus 50 illustrated in FIGS. 5 and 6. Sender/receiver assemblies 70, such as transducers like the piezoelectric platens as described above, are affixed to either end to measure the velocity parallel, perpendicular and 45° to the bedding (30° for a dodecagonal-shaped specimen). The hydraulic rams are activated so as to apply a confining stress, independent axial loading stress, or pressure on the specimen, which can be monitored by load cells 68. The confining pressure is generally from about 0 to about 10,000 psi gauge. Different pressures can be applied by the hydraulic ram to test the specimen under different stresses.

Measurement of the acoustic wave velocity through rock during the performance of other type testing have shown that as the stress (hydrostatic and/or deviatoric) applied to the specimen is increased, the velocity will increase above that measured in the unconfined (unstressed) condition. As stress is increased, the velocity will increase and achieve a stable value until the stress exceeds the strength of the specimen.

Often the velocity measurements will be performed under hydrostatic condition of 100 psi, 1000 psi, 3000 psi and so on until the estimated underground stress magnitude (the net effective stress in the subterranean formation from which the core specimen was obtained) is achieved. Additional testing at higher stress conditions may be performed to evaluate the effect of formation fluid depletion and associated effective stress increases in the subsurface reservoir conditions.

Sender/receiver assemblies 70 are then activated to send ultrasonic waves through the specimens. The waves from one sender/receiver assembly 70 are detected by the sender/receiver assembly 70 on the opposing face. The sender/receiver assemblies 70 can be systematically activated such that ultrasonic wave velocities are introduced into each of the faces of the specimen, all ten faces for the octagonal-shaped specimen. Thus, this method involves measuring the travel time of ultrasonic waves propagating through the specimen. Velocities are found from the travel times and elastic properties (such as Young's modulus and Poisson's ratio) are then calculated from the velocities.

Thus, the octagonal-shaped specimen is used to measure anisotropy at every 45° (every 30° for a dodecagonal-shaped specimen). Most acoustic anisotropy experiments measure only three directions, since the measurements have an assumption that each opposite direction must have the same results. However, natural rocks mostly possess different mineral particle sizes, pore sizes, and mineral elongations. The physical features in rocks generate different wave velocities, and these differences based on heterogeneity are usually smaller than those of anisotropy.

Generally, the pulse-transmissions use waves near 1 MHz frequency on specimens a few centimeters in dimension. Using piezoelectric ceramics, ultrasonic transducers are placed on either face of the specimen in order to generate and record either P- and/or S-waves. A voltage is applied to the transmitting transducer (piezoelectric crystal(s)), which sends a single-frequency pulse through the specimen, while the transducer (piezoelectric crystal(s)) on the opposite end of the specimen supplies a voltage in response to the arrival of the wave. The travel time through the specimen is then determined from the resulting waveform, and this together with knowledge of the length of the specimens is used to calculate the velocity, by calculations known in the art. P-wave and S-wave velocities can be determined for all or a portion of the faces of the specimen and then these velocities can be used to calculate a set of elastic properties that fully describe the material, in accordance with methods known in the art. Because the testing assembly can determine velocities generated at each face, it does not rely on assumptions of symmetry; thus, generating a more accurate description of the material.

In addition to the components shown in the figures, the testing system can include other components for facilitating measurements and calculation of the velocities and elastic properties. Without limitation, these components can include an amplifier, an oscilloscope, a memory, and a computer-processing unit. Thus, each sender/receiver assembly can be connected to an amplifier connected to the oscilloscope and computer-processing unit, which can store data in the memory.

The inventive testing system allows for specimen preparation for most sections of natural rocks including unconventional rocks such as shale with only one specimen required per formation. The in-situ stress conditions can be simulated to investigate the variances of wave velocities for seismic analysis, petrophysics log calibrations, and rock physics research. The options of applying hydrostatic or deviatoric (differential) stress conditions can apply to the specimen.

Additionally, specimen preparation time, loading time, and data interpretation time are relatively shorter than for prior art testing systems. There is no assumption regarding symmetry of the specimen and acoustic anisotropy as well as heterogeneity can be measured simultaneously.

Although certain preferred embodiments of the invention have been herein described in order to illustrate the principles of the invention, it will be understood that various changes and innovations in structure can be effected without departure from these principles. Changes and innovations of this type are therefore deemed to be circumscribed by the spirit and scope of the invention except as the same may be limited by the appended claims or reasonable equivalents thereof.

What is claimed is:

1. A method of measuring ultrasonic wave velocities in a subterranean core specimen having a bedding plane direction, the method comprising:
   introducing the core specimen into a testing system, wherein the core specimen is a polygonal-shaped specimen having at least ten faces such that each face has an associated opposing face to form at least five sets of opposing faces, and the testing system comprises a transducer associated with each face of the polygonal-shaped specimen;
   applying stress to each face of the polygonal-shaped specimen wherein the stress is applied by a plurality of rams with each ram being associated with one of the faces of each set of opposing faces such that the same or different stress are applied to each set of opposing faces;
   monitoring the stress applied to each face;
   introducing an ultrasonic wave to at least one face of the polygonal-shaped specimen;
   detecting the ultrasonic wave on the associated opposing face; and
   calculating wave velocity for the ultrasonic wave based on the detecting of the ultrasonic wave.

2. The method of claim 1, further comprising cutting the core specimen into the polygonal-shaped specimen, wherein two faces run perpendicular to the bedding plane direction and the other faces run parallel to the bedding plane direction.

3. The method of claim 1, further comprising saturating the polygonal-shaped specimen with a gas or a liquid prior to introducing the polygonal-shaped specimen into the testing system.

4. The method of claim 3, wherein the polygonal-shaped specimen is saturated with salt water.

5. The method of claim 1, wherein the step of calculating wave velocity comprises:
   measuring the travel time for each ultrasonic wave; and
   calculating wave velocity for each ultrasonic wave.

6. The method of claim 1, further comprising calculating elastic properties associated with the core specimen.

7. The method of claim 1, wherein in the step of introducing an ultrasonic wave, there are plurality of ultrasonic waves introduced to the polygonal-shaped specimen with one of the ultrasonic waves introduced to each face of the polygonal-shaped specimen and each ultrasonic wave is detected on the associated opposing face of the polygonal-shaped specimen.

8. The method of claim 7, wherein the introduction of the plurality of ultrasonic waves is performed sequentially among the faces of the polygonal-shaped specimen.

9. The method of claim 7, wherein the introduction of the plurality of ultrasonic waves is performed simultaneously on two or more faces of the polygonal-shaped specimen.

10. The method of claim 7, wherein the step of calculating wave velocity comprises:
    measuring the travel time for each ultrasonic wave;
    calculating wave velocity for each ultrasonic wave; and
    calculating elastic properties associated with the core specimen.

11. The method of claim 10, further comprising saturating the polygonal-shaped specimen with a gas or a liquid prior to introducing the polygonal-shaped specimen into the testing system.

12. The method of claim 11, wherein the polygonal-shaped specimen is saturated with salt water.

13. The method of claim 12, further comprising cutting the core specimen into the polygonal-shaped specimen, wherein two faces run perpendicular to the bedding plane direction and the other faces running parallel to the bedding plane direction.

14. A system for measuring wave velocities in a subterranean core specimen having a bedding plane direction, the system comprising:
    a plurality of rams, configured to apply a stress to a polygonal-shaped core specimen having a set of opposing faces, wherein the polygonal-shaped core specimen has at least ten faces, wherein the polygonal-shaped core specimen is such that each face has an associated opposing face to form at least five sets of opposing faces, and wherein each ram of the plurality of rams is associated in a one-to-one relationship with one of the sets of opposing faces such that each applies stress to the polygonal-shaped core specimen at one of the faces of the associated set of opposing faces;
    an acoustic assembly associated with the set of opposing faces configured to send an acoustic signal into one of the opposing faces and receive a signal from the other opposing face; and
    a load cell associated with a second face of the set of opposing faces, and configured to monitor force applied to the polygonal-shaped core specimen by the ram to the first face.

15. The system of claim 14, wherein the acoustic system comprises piezoelectric crystals associated with each face of a set of opposing faces, and which send and receive acoustic waves across the crystal.

16. The system of claim 14, wherein the rams are associated with half the faces of the polygonal-shaped core specimen.

17. The system of claim 16, wherein the acoustic system comprises piezoelectric crystals associated with each face of a set of opposing faces and which send and receive acoustic waves across the crystal.

* * * * *